(12) United States Patent
Heidemann

(10) Patent No.: US 6,688,165 B2
(45) Date of Patent: Feb. 10, 2004

(54) BALL JOINT WITH WEAR TESTING

(75) Inventor: Manfred Heidemann, Belm-Vehrte (DE)

(73) Assignee: ZF Lemforder Metallwaren AG, Dielingen (DE)

(*) Notice: Subject to any disclaimer, the term of this patent is extended or adjusted under 35 U.S.C. 154(b) by 0 days.

(21) Appl. No.: 10/030,515
(22) PCT Filed: Feb. 27, 2001
(86) PCT No.: PCT/DE01/00732
§ 371 (c)(1), (2), (4) Date: Oct. 22, 2001
(87) PCT Pub. No.: WO01/65130
PCT Pub. Date: Sep. 7, 2001

(65) Prior Publication Data
US 2003/0070476 A1 Apr. 17, 2003

(30) Foreign Application Priority Data
Feb. 28, 2000 (DE) .......................... 100 09 054

(51) Int. Cl.⁷ ............................................. G01M 15/00
(52) U.S. Cl. ....................................... 73/118.1; 73/118.1
(58) Field of Search .......................... 403/11, 133, 134, 403/138, 122; 76/866; 73/118.1

(56) References Cited

U.S. PATENT DOCUMENTS 3,578,365 A * 5/1971 Gottschald et al. ............ 287/87
3,849,009 A * 11/1974 Bourdon ...................... 403/133
5,836,415 A * 11/1998 Barrowman ................. 180/266
6,341,915 B1 * 1/2002 Kammel ..................... 403/135

FOREIGN PATENT DOCUMENTS

| DE | 195 46 084 | 5/1997 | |
| DE | 199 18 869 | 10/1999 | |
| JP | 56006911 | 1/1981 | |
| JP | 62137407 | * 6/1987 | ......... F16C/11/06 |
| JP | 63292001 | 11/1988 | |

* cited by examiner

Primary Examiner—Kamand Cuneo
Assistant Examiner—Monica D. Harrison
(74) Attorney, Agent, or Firm—McGlew and Tuttle, P.C.

(57) ABSTRACT

A ball-and-socket joint, preferably for vehicle suspensions or steering mechanisms of motor vehicles, has a joint housing and a pivot pin, which is mounted rotatably and deflectably in a spherical bearing surface via a one-part or multipart bearing shell. The bearing shell itself is fixed in the joint housing. The joint housing or the pivot pin is fixed against the vehicle suspension in an electrically insulated manner, in which the joint housing (1) and the pivot pin (2) are connected according to a potential difference-measuring unit (13) via electrical contacts (12, 14). The spherical bearing surface of the pivot pin (2) and its corresponding opposite surface in the joint housing (1) are electrically insulated against each other. The state of wear of a ball-and-socket joint can be determined and the user of the motor vehicle can obtain an indication of the end of the service life of the ball-and-socket joint and the necessary repair in time.

14 Claims, 2 Drawing Sheets

BALL JOINT WITH WEAR TESTING

FIELD OF THE INVENTION

The present invention pertains to a ball-and-socket joint, preferably for motor vehicle suspensions or steering mechanisms of motor vehicles with a joint housing and a pivot pin, which is mounted rotatably and deflectably in a one-part or multipart bearing shell by means of a spherical bearing surface, wherein the bearing shell is in turn fixed in the joint housing and wherein the joint housing or the pivot pin is fixed against the vehicle suspension in an electrically insulated manner.

BACKGROUND OF THE INVENTION

Ball-and-socket joints of this type have been known for a long time and are used in large numbers especially in the automotive industry. The ball-and-socket joints installed in a motor vehicle are subject to natural wear due to corresponding stress during the operation of the motor vehicle. The wear limit and the service life of a ball-and-socket joint is reached when the bearing shell arranged between the pivot pin and the housing can no longer assume its bearing function over a large area or partially as a consequence of its wear or other abrasion. Increased wear is frequently the consequence of leaky sealing systems, i.e., for instance, when the sealing bellows was damaged and moisture or contaminants were able to penetrate directly into the interior of the joint as a consequence of this. If the bearing shell is worn off to such an extent, the pivot pin could ultimately even become completely separated from the joint. The function of a ball-and-socket joint whose service life limit has been reached may consequently be substantially limited or lead to total failure, which must not happen especially in the case of ball-and-socket joints used in safety-relevant positions. Such a total failure may have serious consequences for the ability of adjoining components to function and may threaten the life of the user of an affected motor vehicle.

SUMMARY AND OBJECTS OF THE INVENTION

The object of the present invention is therefore to improve a ball-and-socket joint of this type such that the wear on the ball shell of the ball-and-socket joint is indicated by suitable measures, so that timely replacement of the affected ball-and-socket joint can be performed before greater risk potentials develop.

According to the invention, a ball-and-socket joint, preferably for vehicle suspensions or steering mechanisms of motor vehicles, is provided with a joint housing and a pivot pin, which is mounted rotatably and deflectably in a one-part or multipart bearing shell by means of a spherical bearing surface. The bearing shell is in turn fixed in the joint housing. The joint housing or the pivot pin is fixed against the vehicle suspension or the steering mechanism in an electrically insulated manner. Provisions are made for the joint housing and the pivot pin to be connected by means of electrical contacting to a potential difference-measuring unit. The spherical bearing surface of the pivot pin and its corresponding opposite bearing surface in the joint housing are electrically insulated against each other.

This design according to the present invention is such that due to the electrical contact connections between the joint housing and the pivot pin, a potential difference is present in the case of an intact ball-and-socket joint, and this potential difference is eliminated at the moment at which the insulation between the pivot pin and the joint housing is considerably reduced or eliminated as a consequence of wear in an area. This usually happens due to the fact that the bearing shell, which is preferably made of a plastic and is arranged between the pivot pin and the joint housing, is no longer able to assume its insulating function as a consequence of wear in an area. An electrically conductive connection is established at this area between the pivot pin and the joint housing, as a result of which the potential difference between the two components is eliminated. The connected potential difference-measuring means permanently monitors the electrical state of the ball-and-socket joint and in the case of a change in the potential difference, it can activate, e.g., a display device arranged downstream, which can display the necessary repair of the worn ball-and-socket joint to the user of the vehicle.

In addition, the increasing wear of the bearing shell can also be displayed by means of a potential difference-measuring means according to the present invention, so that a replacement of the ball-and-socket joint is also possible already before a metallic contact, i.e., a direct electrical connection.

Within the framework of another special embodiment of the subject of the present invention, the bearing surface of the pivot pin may have an electrically non-conductive coating. This embodiment is necessary when the intercalated bearing shell is unable to assume its insulating function because of a special material selection.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
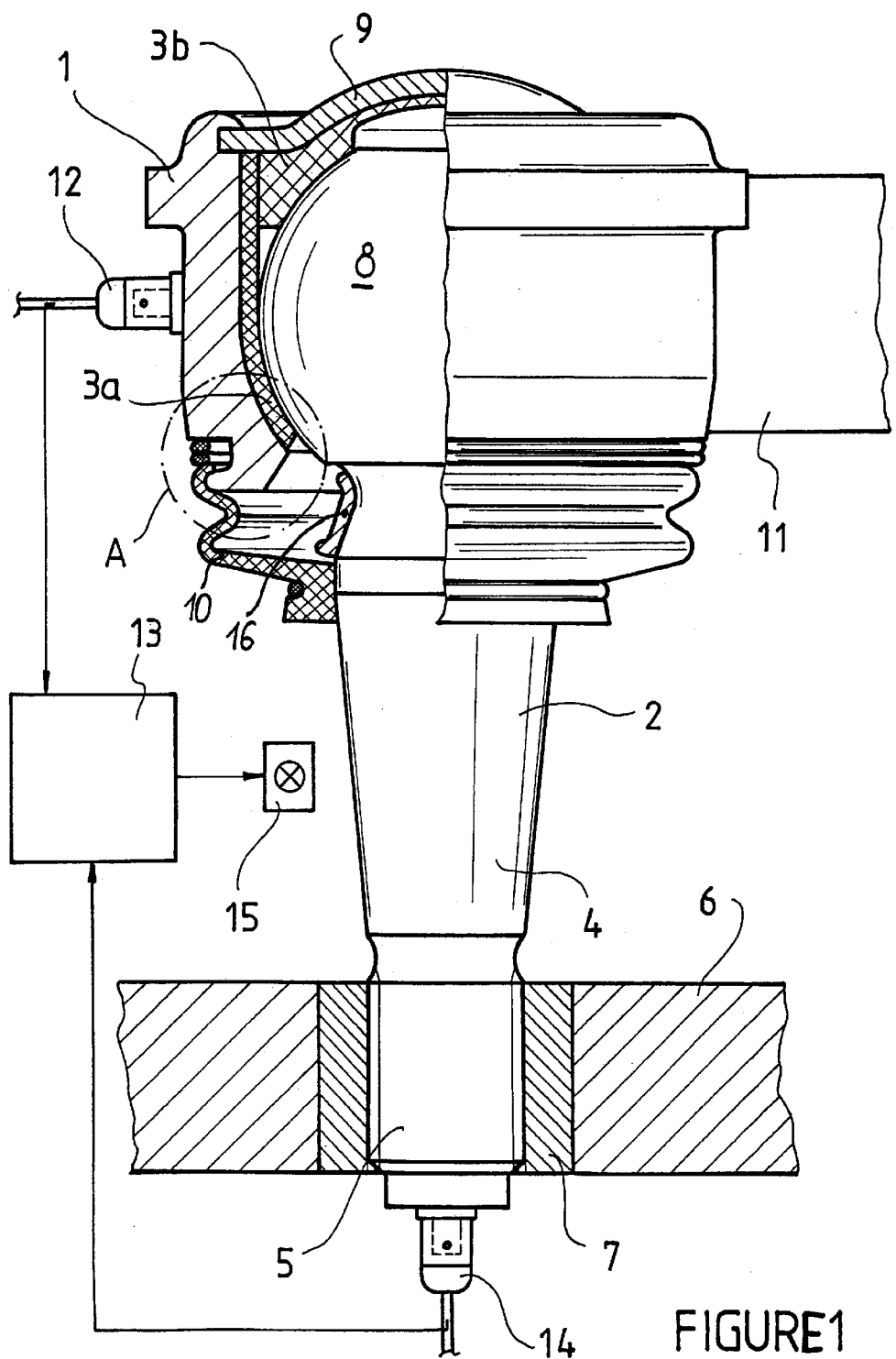
FIG. 1 is a partially sectional view ball-and-socket joint according to the present invention in the installed state on a vehicle suspension.

Referring to the drawings in particular, the ball-and-socket joint shown in FIG. 1 comprises essentially a joint housing 1, a pivot pin 2 and a two-part bearing shell 3a, 3b arranged between the pivot pin 2 and the joint housing 1. The pivot pin 2 has a shaft part 4, which is accommodated in a vehicle body-side carrier 6 by means of a threaded attachment 5. The threaded attachment 5 is mounted in the vehicle body-side carrier 6 via the intermediary of a threaded sleeve 7, which was in turn manufactured from an electrically insulating material, preferably plastic. In addition, other possibilities of insulation are, of course, also conceivable. A spherical bearing surface 8, which is accommodated rotatably and deflectably in the bearing shell, which is designated as a whole by 3 and has a corresponding hollow spherical shape, is accommodated at the end of the shaft part 4 facing away from the threaded attachment 5. The bearing shell 3 is in turn accommodated in the joint housing 1 in an essentially cylindrical hole, wherein the joint housing 1 is closed by a housing cover 9 after the insertion of the bearing shell 3 and the pivot pin 2. At the opposite end of the joint housing 1, a bellows 10 made preferably of rubber is arranged for sealing between the joint housing and the pivot pin 2. For fastening on the vehicle body side, the joint housing 1 has a projection 11, which is shown in FIG. 1 only schematically.

FIG. 1 also shows that an electrical contact 12, which is connected to a potential difference-measuring means 13 via a suitable supply line, is arranged at the joint housing 1. The pivot pin 2 also has at its threaded attachment 5 an electrical contact 14, which is likewise connected to the potential difference-measuring means 13. The potential difference-measuring 5 unit or potential difference-measuring means 13 is shown in FIG. 1 as a black box, because it may be provided, as appreciated by the person skilled in the art, from the state of the art in the conventional manner. A display device 15 is connected as another electrical component to the potential difference-measuring means. To avoid an electrical connection between the pivot pin 2 and the joint housing 1 with the pivot pin deflected to the maximum, the pivot pin has a plastic ring 16, which also positions the bellows 10 at the same time, under the joint ball.

The general view in FIG. 1 shows that due to the insulating properties of the bearing shell 3, which is usually manufactured from a plastic, an electrical insulation is established between the pivot pin 2 and the joint housing 1. The view in FIG. 1 shows the joint housing in the new state, in which the bearing shell 3 can assume its insulating function without problems because of the preset material thickness.

FIG. 2a once again shows detail A from FIG. 1 on a larger scale, because wear problems of a ball-and-socket joint may frequently occur in the area of the closure of the bearing shell. The reference numbers used in FIGS. 2a and 2b correspond to those in FIG. 1. It becomes clear that the bearing shell 3 completely insulates the pivot pin 2 against the joint housing 1 electrically because of its thickness and its material properties.

Figure 2:
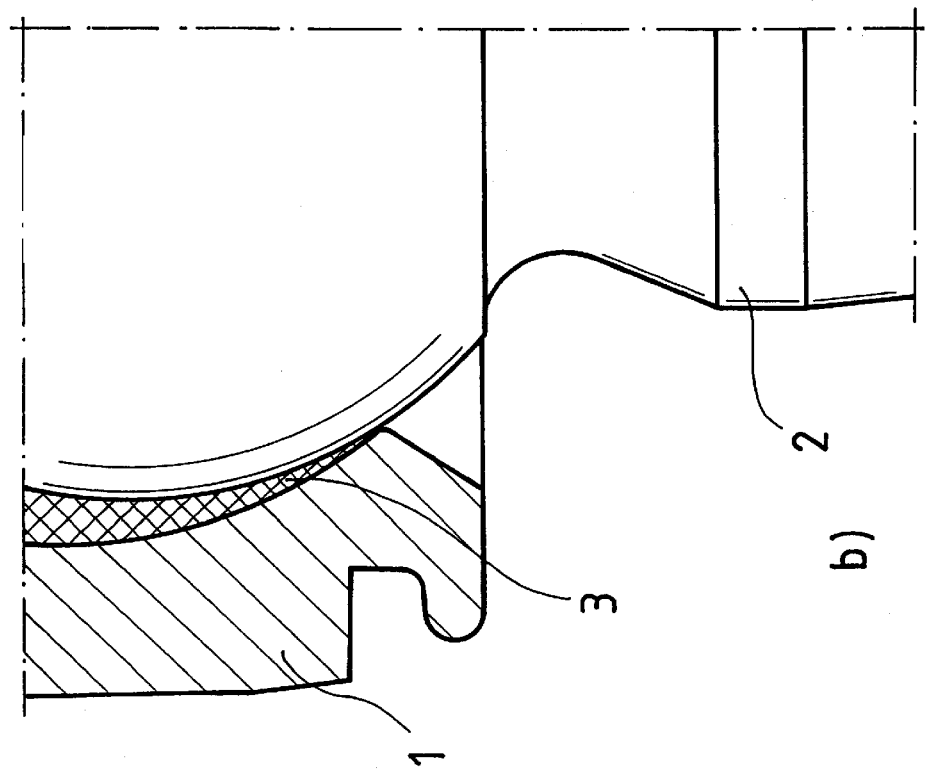
FIG. 2a is an enlarged view of detail A from FIG. 1 in a ball-and-socket joint in the normal state.
FIG. 2b is an enlarged view of detail A from FIG. 1 in a ball-and-socket joint at the end of the service life.
Figure 2:
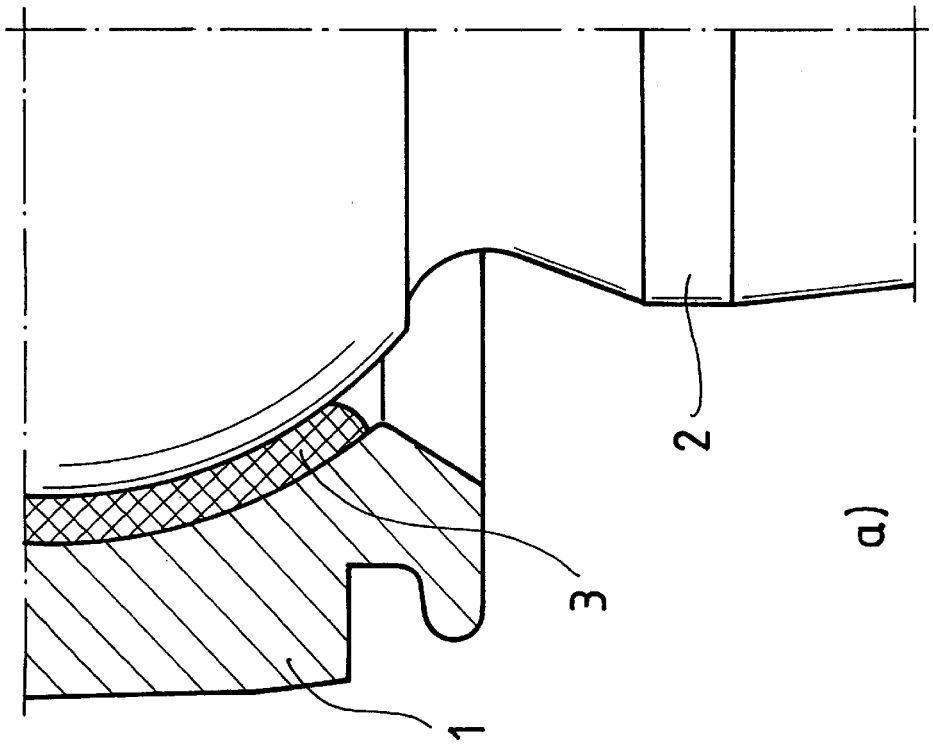

By contrast, FIG. 2b shows that the bearing shell is fully abraded in its end area because of the stress on the ball-and-socket joint, so that the surfaces of the joint housing 1 and the pivot pin 2 are in direct contact with one another in this area. The direct contact between the two components, which originally had a potential difference because of the insulating bearing shell, leads to an equalization of the potentials, which is recorded by the potential difference-measuring means 13. The equalization of the potential difference is then reported by a control signal to the display device, which signals the need to replace the ball-and-socket joint to the user of the vehicle. It is, of course, also conceivable that the bearing shell is manufactured from a material which is not fully insulating. In this case, the reading of the potential difference-measuring means would already drop below a potential difference value $\Delta p_{liem}$ (a threshold value) before the complete abrasion of the bearing shell because of the potential equalization as a consequence of the small thickness of the bearing shell 3. As in the above-described application, in which there is a direct contact between the pivot pin 2 and the pivot housing 1, a value below the limit value would then lead to the activation of the display device. Such a design would have the advantage that replacement of the affected component would be able to be performed already before the immediate service life limit of the ball-and-socket joint is reached, which should certainly be considered to be favorable from the viewpoint of safety.

In addition, it is conceivable to provide the inner area of the joint housing 1 or the bearing surface of the pivot pin 2 with an insulating coating in cases in which the bearing shell 3 is unable to assume its insulating function between the pivot pin 2 and the joint housing 1 because of the necessary material selection. Analogously to the above-described exemplary embodiment, the wear limit would be reached in this case when the coating of the pivot pin would have abraded to the extent that an electrical connection were again present between the two components.

While specific embodiments of the invention have been shown and described in detail to illustrate the application of the principles of the invention, it will be understood that the invention may be embodied otherwise without departing from such principles.

What is claimed is:

1. A ball-and-socket joint preferably for connection to a vehicle suspension or the steering mechanism motor vehicle part, said ball-and-socket joint comprising:
    a joint housing;
    a one-part or multipart bearing shell with a spherical bearing surface, said bearing shell being fixed in said joint housing;
    a pivot pin with a spherical bearing surface mounted rotatably and deflectably in said bearing shell spherical bearing surface, said spherical bearing surface of said pivot pin being electrically insulated with respect to said spherical bearing surface in said joint housing with said bearing surface of said pivot pin having an electrically non-conductive coating, said joint housing or said pivot pin being fixed against the vehicle suspension or the steering mechanism in an electrically insulated;
    a joint housing electrical contact connected to said joint housing;
    a pivot pin electrical contact connected to said pivot pin; and
    a potential difference-measuring means, said joint housing being connected to said potential difference-measuring means by said joint housing electrical contact and said pivot pin being connected to said potential difference-measuring means by said pivot pin electrical contact.

2. A ball-and-socket joint in accordance with claim 1, wherein said bearing shell is arranged between said joint housing and said pivot pin and consists of an electrically non-conductive material.

3. A ball-and-socket joint in accordance with claim 1, further comprising:
    a display device wherein said potential difference-measuring means is coupled with said display device, to which a control signal is sent when the actual potential difference drops below a value $\Delta p_{liem}$.

4. A ball-and-socket joint in accordance with claim 2, further comprising:
    a display device wherein said potential difference-measuring means is coupled with said display device, to which a control signal is sent when the actual potential difference drops below a value $\Delta p_{liem}$.

5. A ball-and-socket joint in accordance with claim 3, further comprising:
    a display device wherein said potential difference-measuring means is coupled with said display device, to which a control signal is sent when the actual potential difference drops below a value $\Delta p_{liem}$.

6. A ball-and-socket joint for connection to a vehicle part said ball-and-socket joint comprising:

a joint housing;

a bearing shell with a spherical bearing surface, said bearing shell being fixed in said joint housing;

a pivot pin with a shaft part and with a spherical bearing surface mounted in said bearing shell spherical bearing surface with said bearing shell is arranged between said joint housing and said pivot pin, said pivot pin being electrically insulated with respect to said joint housing, one of said joint housing and said pivot pin being fixed to the vehicle part in an electrically insulated manner;

a potential difference-measuring unit;

an electrical connection between said joint housing and said potential difference-measuring unit;

an electrical connection between said pivot pin and said potential difference-measuring unit; and a threaded sleeve connected to said pivot pin shaft part, said threaded sleeve formed of an electrically insulating material.

7. A ball-and-socket joint in accordance with claim 6, wherein said bearing shell is arranged between said joint housing and said pivot pin and consists of an electrically non-conductive material.

8. A ball-and-socket joint in accordance with claim 6, wherein said bearing surface of said pivot pin has an electrically non-conductive coating.

9. A ball-and-socket joint in accordance with claim 6, wherein said potential difference-measuring unit issues a control signal when an actual potential difference drops below a threshold value.

10. A ball-and-socket joint in accordance with claim 6, wherein said threaded sleeve is connected to or forms part of the vehicle part for the connection of said pivot pin to the vehicle part in an electrically insulated manner.

11. A ball-and-socket joint for connection to a vehicle part, said ball-and-socket joint comprising:

a joint housing;

a bearing shell with a spherical bearing surface, said bearing shell being fixed in said joint housing said bearing shell being formed of a material or with a structure that is not fully insulating;

a pivot pin with a spherical bearing surface mounted in said bearing shell spherical bearing surface, said pivot pin being electrically insulated with respect to said joint housing, one of said joint housing and said pivot pin being fixed to the vehicle part in an electrically insulated manner;

a potential difference-measuring unit;

an electrical connection between said joint housing and said potential difference-measuring unit; and an electrical connection between said pivot pin and said potential difference-measuring unit.

12. A ball-and-socket joint for connection to a vehicle part, said ball-and-socket joint comprising:

a joint housing with an insulating coating;

a bearing shell with a spherical bearing s said bearing shell being fixed in said joint housing;

a pivot pin with a spherical bearing surface mounted in said bearing shell spherical bearing surface, said pivot pin being electrically insulated with respect to said joint housing, one of said joint housing and said pivot pin being fixed to the vehicle part in an electrically insulated manner;

a potential difference-measuring unit;

an electrical connection between said joint housing and said potential difference-measuring unit;

an electrical connection between said pivot pin and said potential difference-measuring unit.

13. A ball-and-socket joint in accordance with claim 12, wherein said housing has an inner surface area facing said bearing shell, said insulating coating being provided on said inner surface.

14. A ball-and-socket joint for connection to a vehicle part, said ball-and-socket joint comprising:

a joint housing;

a bearing shell with a spherical bearing surface, said bearing shell being fixed in said joint housing;

a pivot pin with a shaft part and with a spherical bearing surface mounted in said bearing shell spherical bearing surface with said bearing shell is arranged between said joint housing and said pivot pin, said pivot pin being electrically insulated with respect to said joint housing, one of said joint housing and said pivot pin being fixed to the vehicle part in an electrically insulated manner;

a potential difference-measuring unit;

an electrical connection between said joint housing and said potential difference-measuring unit;

an electrical connection between said pivot pin and said potential difference-measuring unit; and an electrically insulating material ring connected to said pivot pin at a transition region of said shaft part adjacent to said spherical bearing surface.

\* \* \* \* \*